(12) United States Patent
Choo et al.

(10) Patent No.: US 11,826,179 B2
(45) Date of Patent: Nov. 28, 2023

(54) METHOD, SYSTEM AND NON-TRANSITORY COMPUTER-READABLE RECORDING MEDIUM FOR MANAGING BIOMETRIC INFORMATION

(71) Applicant: HUINNO, CO., LTD., Seoul (KR)

(72) Inventors: Kwang Jae Choo, Gunpo-si (KR); Jin Won Park, Seoul (KR); Sung Hoon Jung, Busan (KR); Yeong Joon Gil, Seoul (KR)

(73) Assignee: HUINNO, CO., LTD., Seoul (KR)

( * ) Notice: Subject to any disclaimer, the term of this patent is extended or adjusted under 35 U.S.C. 154(b) by 5 days.

(21) Appl. No.: 17/639,334

(22) PCT Filed: Sep. 3, 2020

(86) PCT No.: PCT/KR2020/011853
§ 371 (c)(1),
(2) Date: Feb. 28, 2022

(87) PCT Pub. No.: WO2021/071101
PCT Pub. Date: Apr. 15, 2021

(65) Prior Publication Data
US 2022/0313174 A1 Oct. 6, 2022

(30) Foreign Application Priority Data
Oct. 7, 2019 (KR) .................. 10-2019-0124157

(51) Int. Cl.
*A61B 5/00* (2006.01)
*G16H 50/20* (2018.01)
*A61B 5/24* (2021.01)

(52) U.S. Cl.
CPC ............... *A61B 5/746* (2013.01); *A61B 5/24* (2021.01); *A61B 5/7282* (2013.01); *A61B 5/7425* (2013.01); *G16H 50/20* (2018.01)

(58) Field of Classification Search
CPC ..... A61B 5/746; A61B 5/7282; A61B 5/7425; A61B 5/332; A61B 5/389; A61B 5/7275;
(Continued)

(56) References Cited

U.S. PATENT DOCUMENTS

2017/0258349 A1* 9/2017 Watanabe ............ A61B 5/0245
2018/0353142 A1* 12/2018 Shah .................... A61B 5/0022
(Continued)

FOREIGN PATENT DOCUMENTS

KR 102241797 B1 * 4/2021

*Primary Examiner* — Ryan W Sherwin
(74) *Attorney, Agent, or Firm* — United One Law Group LLC; Kongsik Kim; Jhongwoo Peck (57) ABSTRACT

A method for managing biometric information is provided. The method includes the steps of: determining whether a cardiac disorder event has occurred to a user on the basis of biometric information measured from the user's body and situation information associated with the biometric information; providing alarm information associated with the cardiac disorder event to the user in response to determining that the cardiac disorder event has occurred; and associating a time point of occurrence of the cardiac disorder event with feedback information acquired from the user in response to the provided alarm information.

5 Claims, 3 Drawing Sheets

(58) Field of Classification Search
CPC ..... A61B 5/0006; A61B 5/316; A61B 5/7445; G16H 50/20; G16H 40/67; G16H 50/30
See application file for complete search history.

(56) References Cited

U.S. PATENT DOCUMENTS

| | | | |
|---|---|---|---|
| 2019/0138696 A1* | 5/2019 | Carpenter | G16H 40/67 |
| 2019/0200865 A1* | 7/2019 | Hwang | A61B 5/0205 |
| 2019/0274624 A1* | 9/2019 | Mazlish | A61B 5/0031 |
| 2019/0328316 A1* | 10/2019 | Fontanel | G16H 10/60 |

* cited by examiner

METHOD, SYSTEM AND NON-TRANSITORY COMPUTER-READABLE RECORDING MEDIUM FOR MANAGING BIOMETRIC INFORMATION

CROSS-REFERENCE TO RELATED APPLICATIONS

This application is a National Stage Entry of International Application No. PCT/KR2020/011853 filed on Sep. 3, 2020, which claims priority from Korean Application No. 10-2019-0124157 filed on Oct. 7, 2019. The aforementioned applications are incorporated herein by reference in their entireties.

TECHNICAL FIELD

The present invention relates to a method, system, and non-transitory computer-readable recording medium for managing biometric information.

BACKGROUND

In recent years, smart devices have emerged that allow users to easily and conveniently measure and record biometric information such as an electrocardiogram at home without visiting hospitals. Further, the hospitals can diagnose the presence of cardiac disorders such as arrhythmia on the basis of the recorded biometric information of the users.

As an example of related conventional techniques, Korean Laid-Open Patent Publication No. 2018-120953 discloses fitness-ware capable of providing electromyographic and electrocardiographic changes of a wearer during exercise to an external device, comprising: a plurality of fiber electrode units that are provided in a plurality of holes of the fitness-ware and comprise fiber electrodes, a support member that covers and supports the outer side of the fiber electrodes and is woven in the form of meshes of a fiber material, and an elastic band disposed across one side of the support member to enhance skin contact of the fiber electrodes; a control module that is mounted on one side of the fitness-ware to measure an electrocardiogram and an electromyogram, detects a current generated in the wearer's muscle through the fiber electrode units, and converts the detected current into a digital signal to provide the digital signal to the external device; and a conductive thread pattern unit that electrically connects the fiber electrode units and the control module using electrically conductive threads and is attached to the fitness-ware in a staggered fashion.

However, according to the techniques introduced so far as well as the above-described conventional technique, the user's situation at the time of measuring the biometric information is not known at all, and thus it has often been determined that there is a disorder according to the biometric information, even though there is actually no disorder in the heart of the user. Further, in order to accurately diagnose the presence of a cardiac disorder, feedback is received from the user about the user's situation at the time of occurrence of the cardiac disorder, but it is not easy for the user to remember the situation when the biometric information is later analyzed by medical staff.

In this connection, the inventor(s) present a novel and inventive technique for accurately diagnosing the presence of a cardiac disorder of a user by monitoring a cardiac disorder event of the user on the basis of biometric information measured from the user's body and situation information associated with the biometric information, and associating a time point of occurrence of the cardiac disorder event with feedback provided from the user when the cardiac disorder event has occurred.

SUMMARY

One object of the present invention is to solve all the above-described problems in the prior art.

Another object of the invention is to provide assistance for accurately analyzing and diagnosing the presence of a cardiac disorder by monitoring and actively notify a user of the occurrence of a cardiac disorder event, and associating a time point of occurrence of the cardiac disorder event with feedback provided from the user when the cardiac disorder event has occurred.

Yet another object of the invention is to accurately monitor the occurrence of a cardiac disorder event by analyzing a user's biometric information and situation information associated therewith together.

Still another object of the invention is to provide assistance for accurately analyzing and diagnosing the presence of a cardiac disorder by synchronizing, recording, and displaying biometric information associated with a cardiac disorder event, situation information associated with the cardiac disorder event, and feedback information associated with the cardiac disorder event.

The representative configurations of the invention to achieve the above objects are described below.

According to one aspect of the invention, there is provided a method for managing biometric information, the method comprising the steps of: determining whether a cardiac disorder event has occurred to a user on the basis of biometric information measured from the user's body and situation information associated with the biometric information; providing alarm information associated with the cardiac disorder event to the user in response to determining that the cardiac disorder event has occurred; and associating a time point of occurrence of the cardiac disorder event with feedback information acquired from the user in response to the provided alarm information.

According to another aspect of the invention, there is provided a system for managing biometric information, the system comprising: an event management unit configured to determine whether a cardiac disorder event has occurred to a user on the basis of biometric information measured from the user's body and situation information associated with the biometric information; an alarm information management unit configured to provide alarm information associated with the cardiac disorder event to the user in response to determining that the cardiac disorder event has occurred; and a time point management unit configured to associate a time point of occurrence of the cardiac disorder event with feedback information acquired from the user in response to the provided alarm information.

In addition, there are further provided other methods and systems to implement the invention, as well as non-transitory computer-readable recording media having stored thereon computer programs for executing the methods.

According to the invention, it is possible to accurately analyze and diagnose the presence of a cardiac disorder by monitoring and actively notify a user of the occurrence of a cardiac disorder event, and associating a time point of occurrence of the cardiac disorder event with feedback provided from the user when the cardiac disorder event has occurred.

According to the invention, it is possible to accurately monitor the occurrence of a cardiac disorder event by analyzing a user's biometric information and situation information associated therewith together.

According to the invention, it is possible to accurately analyze and diagnose the presence of a cardiac disorder by synchronizing, recording, and displaying biometric information associated with a cardiac disorder event, situation information associated with the cardiac disorder event, and feedback information associated with the cardiac disorder event.

DETAILED DESCRIPTION

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures and characteristics described herein may be implemented as modified from one embodiment to another without departing from the spirit and scope of the invention. Furthermore, it shall be understood that the positions or arrangements of individual elements within each embodiment may also be modified without departing from the spirit and scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, various preferred embodiments of the present invention will be described in detail with reference to the accompanying drawings to enable those skilled in the art to easily implement the invention.
Configuration of the Entire System FIG. 1 schematically shows the configuration of the entire system for managing biometric information according to one embodiment of the invention.

Figure 1:
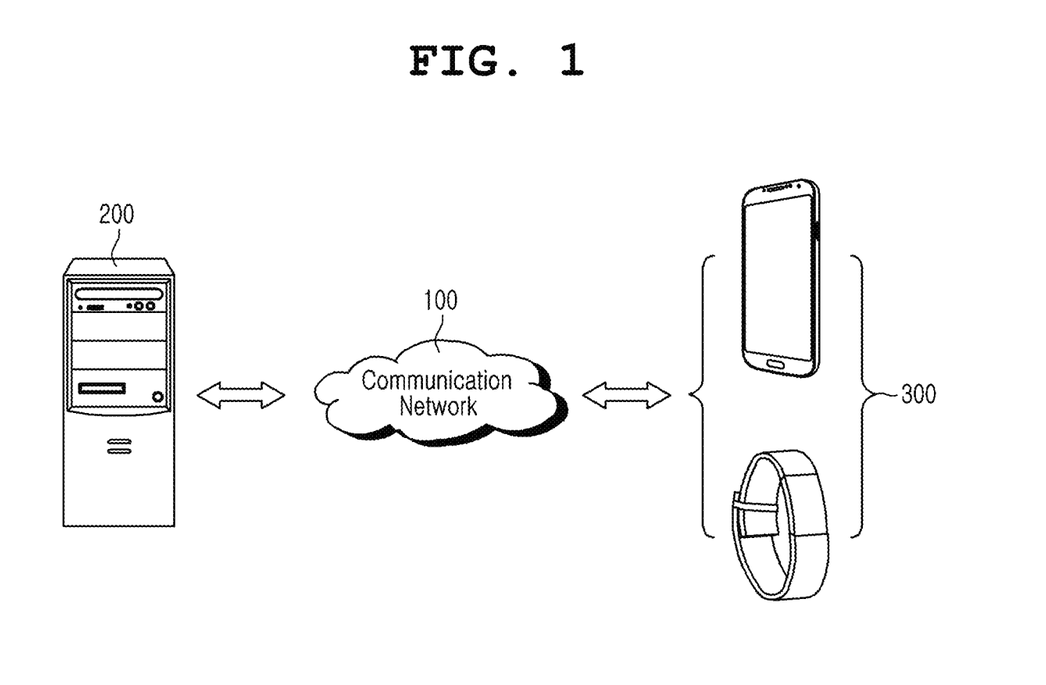
FIG. 1 schematically shows the configuration of an entire system for managing biometric information according to one embodiment of the invention.

As shown in FIG. 1, the entire system according to one embodiment of the invention may comprise a communication network 100, a biometric information management system 200, and a device 300.

First, the communication network 100 according to one embodiment of the invention may be implemented regardless of communication modality such as wired and wireless communications, and may be constructed from a variety of communication networks such as local area networks (LANs), metropolitan area networks (MANs), and wide area networks (WANs). Preferably, the communication network 100 described herein may be the Internet or the World Wide Web (WWW). However, the communication network 100 is not necessarily limited thereto, and may at least partially include known wired/wireless data communication networks, known telephone networks, or known wired/wireless television communication networks.

For example, the communication network 100 may be a wireless data communication network, at least a part of which may be implemented with a conventional communication scheme such as radio frequency (RF) communication, WiFi communication, cellular communication (e.g., Long Term Evolution (LTE) communication), Bluetooth communication (more specifically, Bluetooth Low Energy (BLE) communication), infrared communication, and ultrasonic communication.

Next, the biometric information management system 200 according to one embodiment of the invention may be a digital device having a memory means and a microprocessor for computing capabilities. The biometric information management system 200 may be a server system.

The biometric information management system 200 according to one embodiment of the invention may function to: determine whether a cardiac disorder event has occurred to a user on the basis of biometric information measured from the user's body and situation information associated with the biometric information; provide alarm information associated with the cardiac disorder event to the user in response to determining that the cardiac disorder event has occurred; and associate a time point of occurrence of the cardiac disorder event with feedback information acquired from the user in response to the provided alarm information.

The cardiac disorder event according to one embodiment of the invention may include various cardiac disorder events associated with arrhythmia, such as premature atrial complex, premature ventricular complex, atrial fibrillation, atrial flutter, multifocal atrial tachycardia, paroxysmal supraventricular tachycardia, Wolf-Parkinson-White syndrome, ventricular tachycardia, ventricular fibrillation, and atrioventricular (AV) block. Meanwhile, it is noted that the cardiac disorder event according to one embodiment of the invention is not necessarily limited to those associated with arrhythmia as mentioned above, but may be changed to various cardiac disorder events associated with heart health, such as cardiac arrest.

The configuration and functions of the biometric information management system 200 according to the invention will be discussed in more detail below. Meanwhile, although the biometric information management system 200 has been described as above, the above description is illustrative, and it will be apparent to those skilled in the art that at least a part of the functions or components required for the biometric information management system 200 may be implemented or included in the device 300 to be described below or an external system (not shown), as necessary.

Next, according to one embodiment of the invention, the device 300 is digital equipment that may function to connect to and then communicate with the biometric information management system 200 via the communication network 100, and any type of portable digital equipment having a memory means and a microprocessor for computing capabilities, such as a smart phone and a tablet PC, may be adopted as the device 300 according to the invention. Further, according to one embodiment of the invention, the device 300 may include a biometric information measurement sensor for acquiring biometric information from the user's body (e.g., an electrocardiogram sensor, an electromyogram sensor, a heart rate sensor, a brainwave sensor, a pulse sensor) or a position/motion detection sensor for acquiring situation information of the user (e.g., a GPS sensor, an acceleration sensor, and a gyroscope sensor).

Meanwhile, it is noted that the above biometric information measurement sensor or position/motion detection sensor according to one embodiment of the invention may be included in a wearable device 400 to be described below.

Meanwhile, the device 300 according to one embodiment of the invention may include an application for supporting the functions of managing biometric information according to the invention. The application may be downloaded from the biometric information management system 200 or an external application distribution server (not shown).

Configuration of the Biometric Information Management System

Hereinafter, the internal configuration of the biometric information management system 200 crucial for implementing the invention and the functions of the respective components thereof will be discussed.

Figure 2:
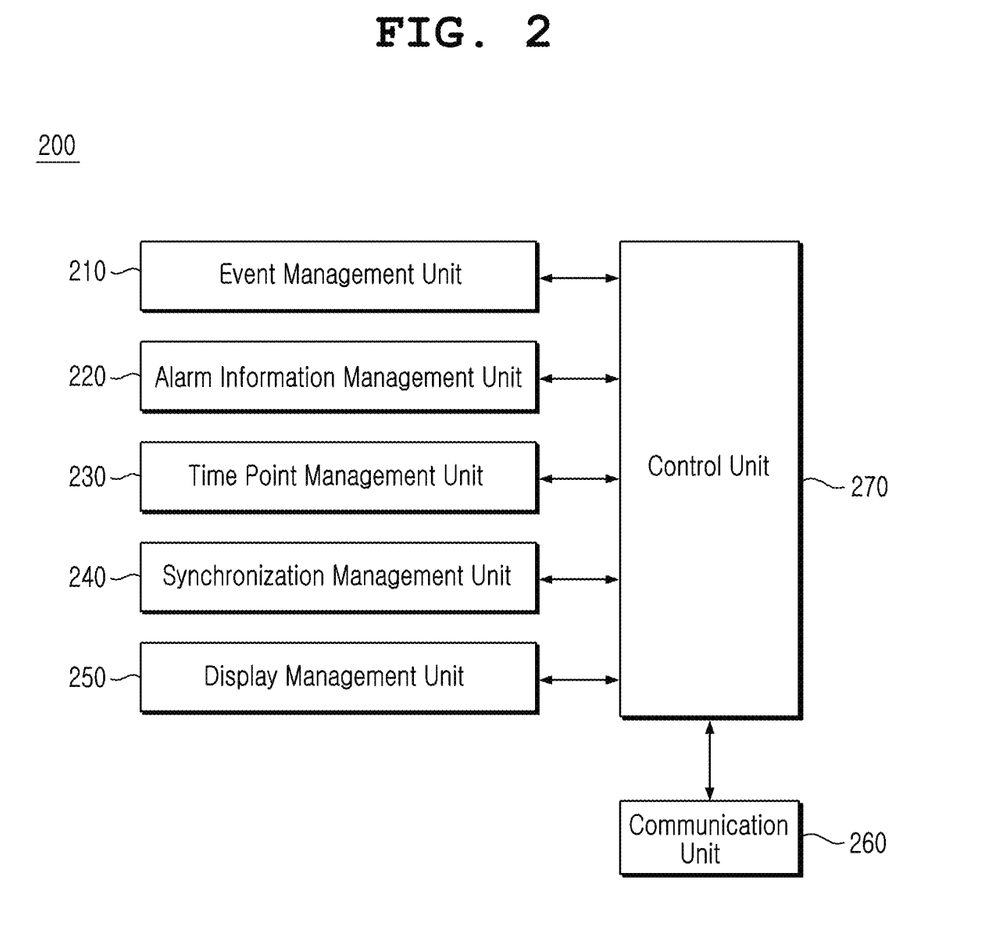
FIG. 2 specifically shows the internal configuration of a biometric information management system according to one embodiment of the invention.

FIG. 2 specifically shows the internal configuration of the biometric information management system 200 according to one embodiment of the invention.

As shown in FIG. 2, the biometric information management system 200 according to one embodiment of the invention may comprise an event management unit 210, an alarm information management unit 220, a time point management unit 230, a synchronization management unit 240, a display management unit 250, a communication unit 260, and a control unit 270. According to one embodiment of the invention, at least some of the event management unit 210, the alarm information management unit 220, the time point management unit 230, the synchronization management unit 240, the display management unit 250, the communication unit 260, and the control unit 270 may be program modules that communicate with an external system. The program modules may be included in the biometric information management system 200 in the form of operating systems, application program modules, and other program modules, while they may be physically stored in a variety of commonly known storage devices. Further, the program modules may also be stored in a remote storage device that may communicate with the biometric information management system 200. Meanwhile, such program modules may include, but are not limited to, routines, subroutines, programs, objects, components, and data structures for performing specific tasks or executing specific abstract data types according to the invention as will be described below.

First, the event management unit 210 according to one embodiment of the invention may determine whether a cardiac disorder event has occurred to a user on the basis of biometric information measured from the user's body and situation information associated with the biometric information. The biometric information according to one embodiment of the invention may include a variety of biometric information (particularly, biometric information that may be associated with cardiac disorders) such as an electrocardiogram, heart rate, brain wave, and pulse. Further, the situation information associated with the biometric information according to one embodiment of the invention implies the user's situation specified at a time point at which the biometric information is measured from the user's body, or specified at a predetermined time before or after the time point, and may encompass the user's action, motion, and posture. For example, according to one embodiment of the invention, the situation information may be acquired by analyzing information acquired from at least one of a GPS sensor (e.g., for taking account of the user's position in the process of specifying the situation information), an acceleration sensor, and a gyroscope sensor of the device 300 owned by the user or another device (not shown) (e.g., the wearable device 400) connected to the device 300 via the communication network 100.

For example, the event management unit 210 according to one embodiment of the invention may determine whether a cardiac disorder event has occurred to the user by extracting at least one feature (e.g., P-wave period, Q-T interval, etc.) associated with the cardiac disorder event from the above biometric information, and analyzing the at least one extracted feature on the basis of the user's situation (e.g., the user's action or posture) specified from the above situation information. More specifically, when it is determined that the user is running on a road on the basis of the situation information, the event management unit 210 according to one embodiment of the invention may determine whether a cardiac disorder event has occurred to the user by analyzing whether at least one feature extracted from the biometric information matches with at least one pattern that may appear in an action equal or similar to running. (A lookup table for such a pattern may be predetermined or machine-learned.)

As another example, the event management unit 210 according to one embodiment of the invention may primarily determine whether a cardiac disorder event has occurred to the user by extracting at least one feature associated with the cardiac disorder event from the biometric information, and analyzing the at least one feature (i.e., primary determination). Then, the event management unit 210 according to one embodiment of the invention may verify whether there is any possibility of determining that the cardiac disorder event has not actually occurred to the user, with reference to the user's situation (e.g., the user's action or posture) specified from the above situation information, and may determine that the cardiac disorder event has occurred to the user when the verification is completed (i.e., secondary determination).

Next, when the event management unit 210 determines that the cardiac disorder event has occurred, the alarm information management unit 220 according to one embodiment of the invention may provide alarm information associated with the cardiac disorder event to the user.

For example, the alarm information management unit 220 according to one embodiment of the invention may provide the user with at last one of information on a time and date when the cardiac disorder event has occurred, information on a type of occurrence of the cardiac disorder event (e.g., ventricular fibrillation), and situation information associated with the cardiac disorder event as the alarm information.

Next, the time point management unit 230 according to one embodiment of the invention may function to associate a time point of occurrence of the cardiac disorder event with feedback information acquired from the user in response to the alarm information provided by the alarm information management unit 220. The feedback information according to one embodiment of the invention may include information (e.g., text, audio, video, etc.) entered or provided by the user about the user's situation (e.g., the user's action, motion, or posture) at the time point of occurrence of the cardiac disorder event.

For example, when the feedback information of the user is acquired in response to the alarm information, the time point management unit 230 according to one embodiment of the invention may tag the time point of occurrence of the cardiac disorder event to the feedback information associated with the cardiac disorder event.

As another example, when the feedback information of the user is acquired in response to the alarm information, the time point management unit 230 according to one embodiment of the invention may set a time point of the feedback information as the time point of occurrence of the cardiac disorder event.

Next, when the time point management unit 230 associates the feedback information with the time point of occurrence of the cardiac disorder event, the synchronization management unit 240 according to one embodiment of the invention may synchronize and record the biometric information associated with the cardiac disorder event, the situation information associated with the cardiac disorder event, and the feedback information associated with the cardiac disorder event.

Specifically, when the time point management unit 230 associates the feedback information with the time point of occurrence of the cardiac disorder event, the synchronization management unit 240 according to one embodiment of the invention may synchronize and record the biometric information associated with the cardiac disorder event (e.g., the biometric information during a predetermined time period from before to after the time point of occurrence of the cardiac disorder event), the situation information associated with the cardiac disorder event (e.g., the situation information during a predetermined time period from before to after the time point of occurrence of the cardiac disorder event), and the feedback information associated with the cardiac disorder event (e.g., the feedback information acquired from the user in response to the alarm information associated with the cardiac disorder event), with respect to the time point of occurrence of the cardiac disorder event.

For example, the synchronization management unit 240 according to one embodiment of the invention may group and record the biometric information associated with the cardiac disorder event, the situation information associated with the cardiac disorder event, and the feedback information associated with the cardiac disorder event, with respect to the time point of occurrence of the cardiac disorder event.

As another example, the synchronization management unit 240 according to one embodiment of the invention may synchronize and record each of time points of the biometric information associated with the cardiac disorder event, the situation information associated with the cardiac disorder event, and the feedback information associated with the cardiac disorder event, with the time point of occurrence of the cardiac disorder event.

Next, when the time point management unit 230 associates the feedback information with the time point of occurrence of the cardiac disorder event, the display management unit 250 according to one embodiment of the invention may cause two or more of the biometric information associated with the cardiac disorder event, the situation information associated with the cardiac disorder event, and the feedback information associated with the cardiac disorder event to be displayed together.

For example, the display management unit 250 according to one embodiment of the invention may cause the biometric information associated with the cardiac disorder event (e.g., an electrocardiogram at the time point of occurrence of the cardiac disorder event or at a predetermined time before or after the time point), the situation information associated with the cardiac disorder event (e.g., information on an action of the user running at the time point of occurrence of the cardiac disorder event), and the feedback information associated with the cardiac disorder event (e.g., information entered by the user to indicate that the user is running at the time point of occurrence of the cardiac disorder event), which are synchronized with respect to the time point of occurrence of the cardiac disorder event, to be provided together on a display.

Next, the communication unit 260 according to one embodiment of the invention may function to enable data transmission/reception from/to the event management unit 210, the alarm information management unit 220, the time point management unit 230, the synchronization management unit 240, and the display management unit 250.

Lastly, the control unit 270 according to one embodiment of the invention may function to control data flow among the event management unit 210, the alarm information management unit 220, the time point management unit 230, the synchronization management unit 240, the display management unit 250, and the communication unit 260. That is, the control unit 270 may control data flow into/out of the biometric information management system 200 or data flow among the respective components of the biometric information management system 200, such that the event management unit 210, the alarm information management unit 220, the time point management unit 230, the synchronization management unit 240, the display management unit 250, and the communication unit 260 may carry out their particular functions, respectively.

Figure 3:
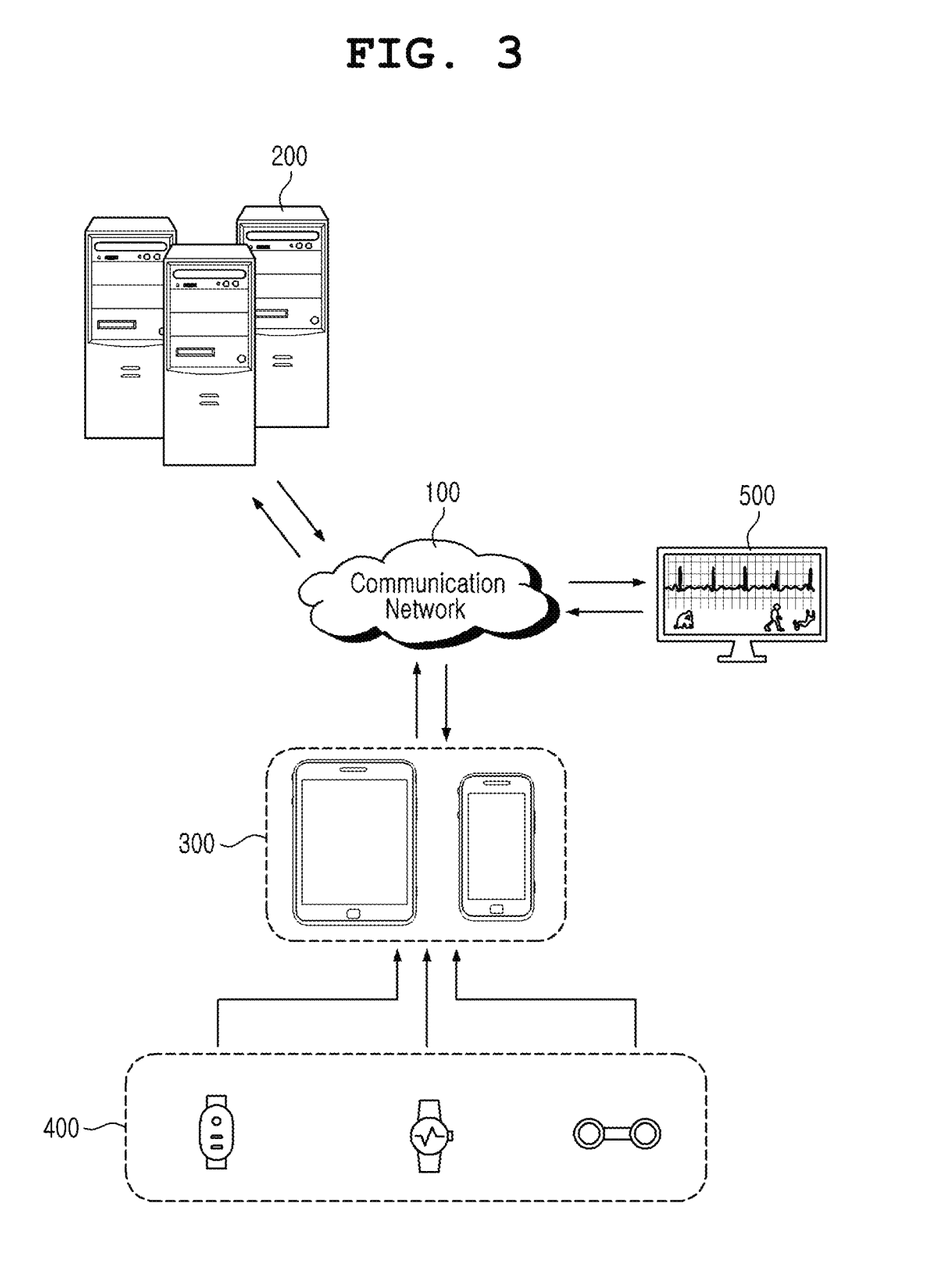
FIG. 3 illustratively shows a process of managing biometric information according to one embodiment of the invention.

FIG. 3 illustratively shows a process of managing biometric information according to one embodiment of the invention.

Referring to FIG. 3, according to one embodiment of the invention, it may be assumed that a smart phone 300 (i.e., the device 300 according to the invention) is connected to a wearable device 400, and the wearable device 400 acquires biometric information from a user's body or acquires and provides the smart phone 300 with situation information associated with the biometric information or information for specifying the situation information (e.g., acceleration information related to the user's motion). Here, the wearable device 400 according to one embodiment of the invention is digital equipment that may function to connect to and then communicate with the smart phone 300 or the biometric information management system 200 via the communication network 100, and may include a variety of equipment (e.g., a smart watch, a wireless patch, etc.) that may be directly or indirectly attached to the user's body to acquire biometric information or situation information from the user.

First, according to one embodiment of the invention, the wearable device 400 may acquire biometric information measured from the user's body and acceleration information at the time of measuring the biometric information (or during a predetermined time period from before to after the time of measuring).

Next, according to one embodiment of the invention, the wearable device 400 may provide the biometric information and the acceleration information to the smart phone 300, and the smart phone 300 may deliver the biometric information and the acceleration information to the biometric information management system 200.

Next, according to one embodiment of the invention, the biometric information management system 200 may specify situation information associated with the acceleration information from the acceleration information.

Next, according to one embodiment of the invention, the biometric information management system 200 may determine whether a cardiac disorder event has occurred to the user on the basis of the biometric information and the situation information.

Next, according to one embodiment of the invention, alarm information associated with the cardiac disorder event may be provided to the user in response to determining that the cardiac disorder event has occurred to the user.

For example, according to one embodiment of the invention, the alarm information may be provided to the user via the smart phone 300 or the wearable device 400.

Next, according to one embodiment of the invention, feedback information provided from the user in response to the provided alarm information may be acquired.

Next, according to one embodiment of the invention, the acquired feedback information may be associated with a time point of occurrence of the cardiac disorder event.

Next, according to one embodiment of the invention, the biometric information associated with the cardiac disorder event, the situation information associated with the cardiac disorder event, and the feedback information associated with the cardiac disorder event may be synchronized with each other and recorded.

For example, according to one embodiment of the invention, the biometric information associated with the cardiac disorder event, the situation information associated with the cardiac disorder event, and the feedback information associated with the cardiac disorder event may be synchronized with respect to the time point of occurrence of the cardiac disorder event, and recorded in the biometric information management system 200 or the smart phone 300.

Next, according to one embodiment of the invention, a hospital's monitor 500 connected to the biometric information management system 200 via the communication network 100 may display the biometric information associated with the cardiac disorder event, the situation information associated with the cardiac disorder event, and the feedback information associated with the cardiac disorder event together.

Through the above process, the hospital may check the biometric information associated with the cardiac disorder event, the situation information associated with the cardiac disorder event, and the feedback information associated with the cardiac disorder event together, with respect to the time point of occurrence of the cardiac disorder event, so that the presence of a cardiac disorder of the user may be more accurately diagnosed.

The embodiments according to the invention as described above may be implemented in the form of program instructions that can be executed by various computer components, and may be stored on a computer-readable recording medium. The computer-readable recording medium may include program instructions, data files, and data structures, separately or in combination. The program instructions stored on the computer-readable recording medium may be specially designed and configured for the present invention, or may also be known and available to those skilled in the computer software field. Examples of the computer-readable recording medium include the following: magnetic media such as hard disks, floppy disks and magnetic tapes; optical media such as compact disk-read only memory (CD-ROM) and digital versatile disks (DVDs); magneto-optical media such as floptical disks; and hardware devices such as read-only memory (ROM), random access memory (RAM) and flash memory, which are specially configured to store and execute program instructions. Examples of the program instructions include not only machine language codes created by a compiler, but also high-level language codes that can be executed by a computer using an interpreter. The above hardware devices may be changed to one or more software modules to perform the processes of the present invention, and vice versa.

Although the present invention has been described above in terms of specific items such as detailed elements as well as the limited embodiments and the drawings, they are only provided to help more general understanding of the invention, and the present invention is not limited to the above embodiments. It will be appreciated by those skilled in the art to which the present invention pertains that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. A method for managing biometric information, comprising:
   determining whether a cardiac disorder event has occurred to a user on the basis of biometric information measured from the user's body and situation information associated with the biometric information;
   providing alarm information associated with the cardiac disorder event to the user in response to determining that the cardiac disorder event has occurred;
   associating a time point of occurrence of the cardiac disorder event with feedback information acquired from the user in response to the provided alarm information, wherein the feedback information includes information entered or provided by the user about the user's situation at the time point of occurrence of the cardiac disorder event, the user's situation including at least posture; and
   synchronizing and recording the biometric information associated with the cardiac disorder event, the situation information associated with the cardiac disorder event, and the feedback information associated with the cardiac disorder event, with respect to the time point of occurrence of the cardiac disorder event, when the feedback information is associated with the time point of occurrence of the cardiac disorder event.

2. The method of claim 1, further comprising:
   causing the biometric information associated with the cardiac disorder event, the situation information associated with the cardiac disorder event, and the feedback information associated with the cardiac disorder event to be displayed together, when the feedback information is associated with the time point of occurrence of the cardiac disorder event.

3. The method of claim 1, wherein the determining step comprises:
   extracting at least one feature associated with the cardiac disorder event from the biometric information; and
   analyzing the at least one extracted feature with reference to the user's situation specified from the situation information, thereby determining whether the cardiac disorder event has occurred to the user.

4. A non-transitory computer-readable recording medium having stored thereon a computer program for executing the method of claim 1.

5. A system for managing biometric information, the system comprising a microprocessor, wherein the microprocessor is configured to:
   determine whether a cardiac disorder event has occurred to a user on the basis of biometric information measured from the user's body and situation information associated with the biometric information;

provide alarm information associated with the cardiac disorder event to the user in response to determining that the cardiac disorder event has occurred;

associate a time point of occurrence of the cardiac disorder event with feedback information acquired from the user in response to the provided alarm information, wherein the feedback information includes information entered or provided by the user about the user's situation at the time point of occurrence of the cardiac disorder event, the user's situation including at least posture; and synchronize and record the biometric information associated with the cardiac disorder event, the situation information associated with the cardiac disorder event, and the feedback information associated with the cardiac disorder event, with respect to the time point of occurrence of the cardiac disorder event, when the feedback information is associated with the time point of occurrence of the cardiac disorder event.

* * * * *